United States Patent
DuBois

[11] Patent Number: 5,902,315
[45] Date of Patent: May 11, 1999

[54] OPTICAL TISSUE DISSECTOR/RETRACTOR

[75] Inventor: Brian R. DuBois, Cincinnati, Ohio

[73] Assignee: Ethicon Endo-Surgery, Inc., Cincinnati, Ohio

[21] Appl. No.: 08/919,975

[22] Filed: Aug. 28, 1997

[51] Int. Cl.⁶ .................................................. A61B 1/32
[52] U.S. Cl. ........................................ 606/190; 600/210
[58] Field of Search ............................... 606/1, 170, 171, 606/180, 190; 600/210, 212

[56] References Cited

U.S. PATENT DOCUMENTS

| | | |
|---|---|---|
| 1,246,338 | 11/1917 | Smit . |
| 2,831,480 | 4/1958 | Milano . |
| 2,840,070 | 6/1958 | Tofflemire . |
| 2,944,552 | 7/1960 | Cannon . |
| 3,651,800 | 3/1972 | Wilbanks . |
| 4,232,660 | 11/1980 | Coles . |
| 4,793,346 | 12/1988 | Mindich . |
| 5,352,219 | 10/1994 | Reddy . |
| 5,373,840 | 12/1994 | Knighton . |
| 5,448,990 | 9/1995 | De Faria-Correa . |
| 5,591,183 | 1/1997 | Chin . |
| 5,601,581 | 2/1997 | Fogarty et al. . |
| 5,607,441 | 3/1997 | Sierocuk et al. . |
| 5,667,480 | 9/1997 | Knight et al. ............................ 606/190 |

FOREIGN PATENT DOCUMENTS

| | | |
|---|---|---|
| 0 642 764 A1 | 3/1995 | European Pat. Off. . |
| 1371689 | 2/1988 | U.S.S.R. . |
| WO 94/09701 | 11/1994 | WIPO . |
| WO 95/10982 | 4/1995 | WIPO . |

OTHER PUBLICATIONS

"Endoscopic Subfascial Discission of Perforating Veins", (G. Hauer et al., Surg Endosc (1988) 2: 5–12).
"A quick and atraumatic method of autologous vein harvesting using the subcutaneous extraluminal dissector", (W.R. Dimitri et al., J Cardiovasc Surg, 1987; 28:103–11).
"Long Saphenous Vein Harvesting", (W. Meldrum–Hanna et al., Aust. N.Z. J. Surg 1986, 56, 923–924).
"Vein Harvest", Alan B. Lumsden & Felmont F. Eaves, III, Endoscopic Plastic Surgery (Quality Medical Publishing, Inc., 1995), pp. 535–543.
"Endoscopic Plastic Surgery", Snowden–Pencer, Inc. (1993 Brochure).
"Instrument for Endoscopic Removal of the Great Saphenous Vein" Endo World 1997, (includes unverified English Translation pp. 2–3).

*Primary Examiner*—William Lewis
*Attorney, Agent, or Firm*—Louis J. Capezzuto

[57] ABSTRACT

A surgical device for dissecting and retracting tissue includes a scope holder for holding an endoscope therein and a transparent concave head connected to the scope holder. The concave head defines a working space therein. A fluid carrying system is operatively connected to and communicates with the concave head and the working space for clearing particulate from the working space.

10 Claims, 8 Drawing Sheets

OPTICAL TISSUE DISSECTOR/RETRACTOR

FIELD AND BACKGROUND OF THE INVENTION

The present invention relates, in general, to tissue dissection and retraction and, in particular, to a new and useful endoscopic method for performing optical tissue dissection and retraction with a novel device that is utilized in carrying out the method in support of a surgical procedure such as a coronary bypass procedure or other type of vessel harvest procedure.

It is a common practice in the surgical field to dissect tissue in order to accommodate various surgical procedures. One type of useful tissue dissector is a balloon dissector such as the device embodied in U.S. Pat. No. 5,607,441. This device is particularly useful for dissecting between tissue layers in order to create space between the dissected layers. Accordingly, it is common to use the balloon dissector in endoscopic surgical procedures such as a laparoscopic hernia repair, laparoscopic bladder neck suspension or lymph node dissection.

Additionally, it has also become common practice to conduct minimally invasive or endoscopic tissue dissection and vessel harvest in a patient in order to facilitate a coronary artery bypass grafting procedure ("CABG"). For instance, vessels such as the saphenous vein are harvested using a minimally invasive tissue dissection method for use in a CABG.

SU 1371689 teaches a vessel removal procedure which utilizes an endoscope having a lumen therethrough. In this procedure, the small saphenous vein is grasped and held with a grasper which is introduced through the lumen of the endoscope. After connective tissue has been dissected from around the vein, the vein is then ligated and transected and removed from the lower limb of the patient through the lumen of the endoscope.

Essentially, the same technique for removal of a vessel is disclosed in U.S. Pat. No. 5,373,840 which pertains to a method for harvesting a vessel such as the saphenous vein. This procedure also utilizes an endoscope having a lumen therethrough which permits the saphenous vein to be grasped by a grasping instrument and dissected. As the vein is withdrawn into the lumen of the endoscope, the endoscope is maneuvered along the length of the vein while side branches of the vein are ligated and transected whenever encountered.

Although this method provides for a minimally invasive technique, there are several drawbacks associated with this procedure. First, in practicing this method, there is limited visibility of the saphenous vein and its side branches because viewing is limited to the immediate area directly in front of the endoscope. Secondly, the illumination within the subcutaneous space created by this type of endoscope is also limited to the light emitted directly at the distal portion of the endoscope. Another drawback to this type of procedure is that the side branches of the saphenous vein limit the maneuverability of the endoscope since the outer edge of the endoscope body is prevented from advancing along the trunk of the saphenous vein until the encountered side branches are ligated and transected thereby. Once freed, the endoscope is then maneuvered until the next side branch is encountered. Moreover, it has been found that methods which utilize this type of endoscope, i.e. an endoscope having a lumen, provide a working space which is very restricted because the side walls of the scope body confine the working instrumentation to a limited area.

Furthermore, the vessel harvesting method described above is typically a three-handed approach which actually requires more than one individual. In this method, one hand is required to hold and maintain the endoscope in position, while a second hand is required to hold the free end of the transected vessel with a grasper and a third hand is required to dissect connective tissue away from the vessel.

Another method for harvesting the saphenous vein is disclosed in "Vein Harvest", Alan B. Lumsden and Felmont F. Eaves, III, in Endoscopic Plastic Surgery (Quality Medical Publishing, Inc., 1995), pp. 535–543. This method provides for performing a preliminary dissection of the saphenous vein while using an open technique prior to inserting an endoscopic retractor such as those commonly used in plastic surgery. A typical endoscopic retractor is the Emory Endoplastic Retractor sold by Snowden-Pencer. In this procedure, once the subcutaneous tissue is retracted with the endoretractor, a pair of disposable 5 mm Metzenbaum laparoscopic scissors are used to dissect the superior surface of the saphenous vein in order to expose the vein. The speed of the dissection of the saphenous vein in this procedure is limited by the spreading motion of the scissor blades as well as the care which must be exercised by the surgeon when dissecting the vein in this manner.

Additionally, it is known to use another type of balloon dissector such as the devices shown in U.S. Pat. Nos. 5,591,183 and 5,601,581 in order to conduct tissue dissection in a patient's leg for harvesting the saphenous vein. These devices and the method for using the devices require placing a cannula into the patient's leg near the saphenous vein and inflating a balloon or plurality of balloons in order to dissect tissue away from the vein for providing space near the vein to facilitate the harvest procedure.

One very successful vessel harvest method is the method developed and promoted by Ethicon Endo-Surgery, Inc., Cincinnati, Ohio. This method utilizes an optical tissue dissector known as the ENDOPATH SUBCU-DISSECTOR™ which is used to separate subcutaneous tissue away from the saphenous vein. There is also an optical tissue retractor known as the ENDOPATH SUBCU-RETRACTOR™ which is used to retract the dissected tissue away from the saphenous vein. Both of these devices utilize a transparent concave working head having a spoon-shape. The concave working head defines a working space that permits instrumentation to be inserted therein in order to facilitate the vessel harvest procedure. Moreover, both of these devices allow an endoscope to be insertably positioned and held at the working head in order to perform tissue dissection and retraction under direct visualization.

Since the transparent working head is used in the warm tissue of patient's leg, there is a tendency for the endoscope lens and the transparent working head to experience condensation or fogging. This is primarily caused by the difference in temperature between the warm moist environment of the patient's leg and the colder, sterile environment of the operating room which tends to be maintained at 60° to 68° F.

The fogging of the working head and the endoscope lens decreases visualization through the endoscope and results in a blurry image of the operating environment within the working space exhibited on the operating room monitor. Thus, it is common for the surgeon or physician assistant to remove the device from the patient's leg in order to clean the endoscope lens or continue with the procedure by introducing a suction device into the working space for clearing the fogging. In either situation, the length of time required to complete the procedure is increased.

Another situation that is sometimes encountered when using the transparent working head, is that it is common to use an energy-based device such as RF electrosurgical scissors or an ultrasonic surgical device such as the ULTRACISION™ LCS Laparoscopic Coagulating Shears manufactured and sold by Ethicon Endo-Surgery, Inc. in order to ligate and transect the side branches of the saphenous vein. Both of these devices are used in the working space defined by the transparent working head.

In cases where an RF electrosurgical device is used, the RF cutting and coagulation of tissue will result in a discharge of smoke that is trapped within the transparent working head resulting in a significant decrease in visibility through the endoscope for the surgeon.

Additionally, for those cases where the ULTRACISION™ device is used, there is a fine mist which is produced and becomes trapped within the transparent working head. This mist has an effect on the surgeon's viewing ability by obscuring visibility within the transparent working head.

Presently, there is no known optical dissection and retraction device that eliminates the problems and inconveniences outlined above.

SUMMARY OF THE INVENTION

The present invention pertains to the dissection and retraction of tissue, and particularly, to a novel surgical device that is used for dissecting and retracting tissue in a minimally invasive surgical procedure.

The surgical device according to the present invention (hereinafter "dissector/retractor") is an optical tissue dissector/retractor as well as a novel method for using the device. The dissector/retractor according to the present invention comprises a scope holder for holding an endoscope therein and a transparent concave head connected to the scope holder wherein the concave head defines a working space therein. A particulate removal system, such as a fluid carrying system, operatively communicates with the concave head and the working space in order to clear particulate from the working space. "Particulate" as defined herein refers to smoke, particles, condensation, mist or the like. The fluid carrying system also clears particulate that collects on the lens of the endoscope. The dissector/retractor also includes a handle which is connected to the scope holder in order to facilitate ease of use and handling during the procedure by the surgeon.

The fluid carrying system according to the present invention includes a scope seal connected to the proximal end of the scope holder and a purge tube which is connected to the scope seal. Both the scope seal and the purge tube are located in the handle. The fluid carrying system further includes a luer connector which connects to a fluid source. A luer seal is located between the luer connector and the purge tube for sealing purposes. Moreover, a gap exists between the endoscope and the scope holder which leads from the scope seal to the concave working head for facilitating the transfer of fluid.

Additionally, the fluid carrying system according to the present invention can be operated in two modes in order to purge particulate from the working space of the optical head as well as the lens of the endoscope. The first mode is a lavage mode in which a fluid flow is provided through the luer connector, the purge tube and the gap between the scope holder and the endoscope for providing the fluid flow directly into the working space as well as about the lens of the endoscope. The second mode is an aspiration mode in which fluid, such as air, can be aspirated through the fluid carrying system in order to purge the device of particulate which ultimately exits the device through the luer connector to an appropriate aspiration source such as vacuum or suction which is connected to the luer connector.

The present invention also includes a novel method for dissecting tissue which comprises the steps of providing the surgical device outlined above. An endoscope is positioned in the scope holder and the surgical device is place in tissue. The tissue is then dissected with the concave head of the device and particulate is purged from the working space of the concave head as well as from around the lens of the endoscope with a fluid flow while the device remains in the tissue. The fluid flow is provided through the fluid carrying system mentioned above in both the lavage mode and the aspiration mode. Either fluid flow mode is selectively chosen by the surgeon.

Moreover, the surgeon also has the option to purge particulate from the working space and the endoscope lens concurrently with the dissection of the tissue. This is easily accomplished by the surgeon by permitting the fluid carrying system to operate and purge particulate during the dissection and retraction of tissue. Alternatively, particulate can be purged from the working space and the endoscope lens at discrete intervals based on the surgeon's preference. Thus, the surgeon can selectively operate the fluid carrying system when desired.

There are several benefits associated with using the novel dissector/retractor according to the present invention and its associated method. For instance, since particulate can be removed from the working space and the endoscope lens while the dissector/retractor remains in tissue, there is a reduction in the number of times that the dissector/retractor is withdrawn and inserted through the incision. By eliminating the need for the surgeon to remove the dissector/retractor from the surgical site in order to clear particulate from the device, there is an overall reduction in the time associated with conducting the surgical procedure. The present invention also assists in eliminating the need to provide additional instruments to the working space.

It is an object of the present invention to provide a dissector/retractor that is simple to use and eliminates some of the problems and/or inconveniences associated with the known tissue dissection and retraction instruments.

The various features of novelty which characterize the invention are pointed out with particularity in the claims annexed to and forming a part of the disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
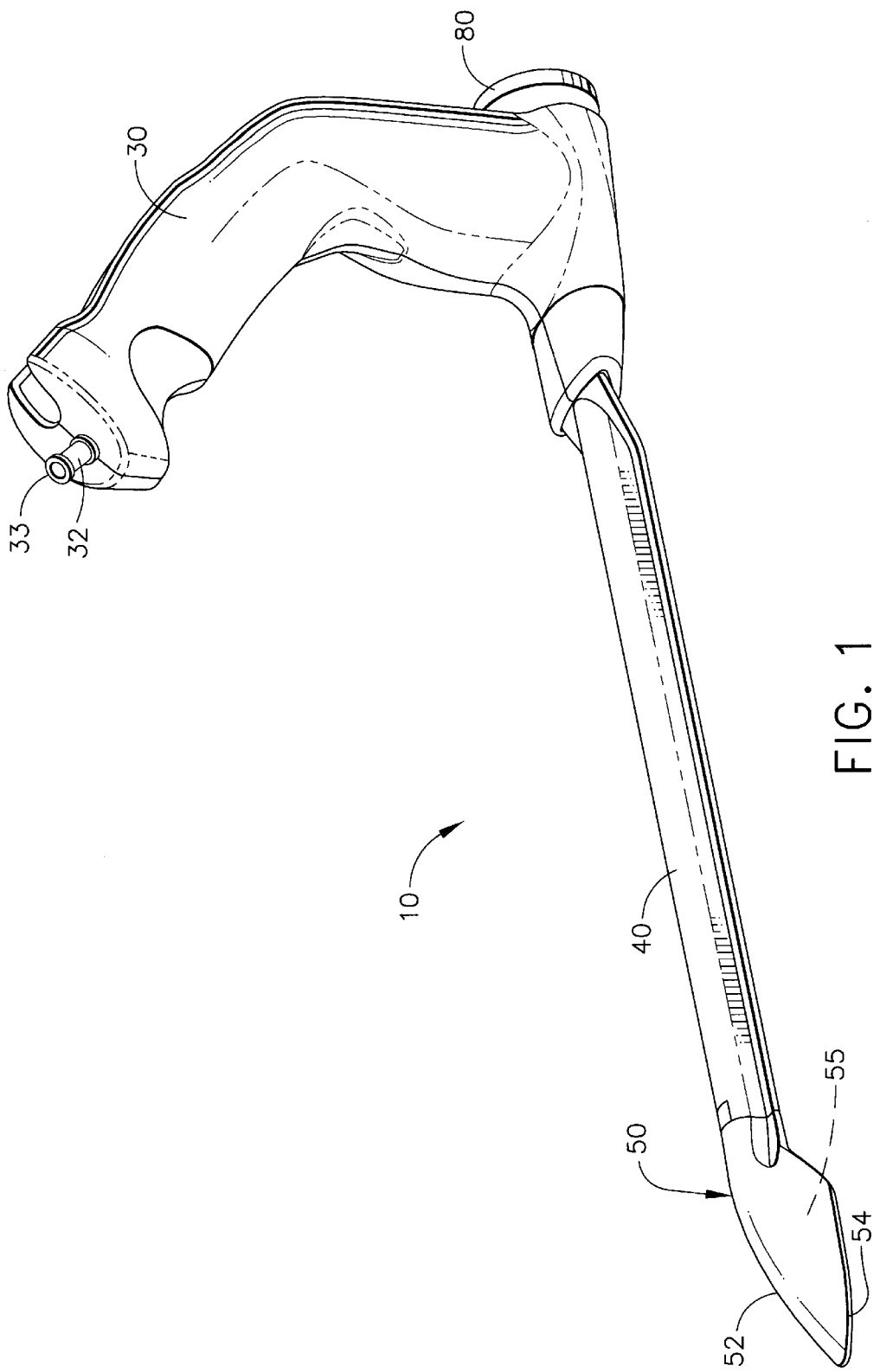
FIG. 1 is a perspective view of a preferred embodiment of an optical tissue dissector/retractor having a particulate removal system according to the present invention.

Referring to FIG. 1, the present invention is an optical tissue dissector/retractor, generally designated 10, comprising a handle 30 located at the proximal end of the dissector/retractor 10. The handle 30 is connected to a cover 40 which longitudinally extends from the handle 30. An optical working head 50 is connected to the cover 40 at the distal end of the dissector/retractor 10 and is positioned opposite the handle 30. The applicant's pending U.S. Patent Applications bearing Ser. Nos.: 08/546,461; 08/698,499; and 08/698,530 relate to the dissector/retractor according to the present invention and are incorporated by reference herein.

Figure 6:
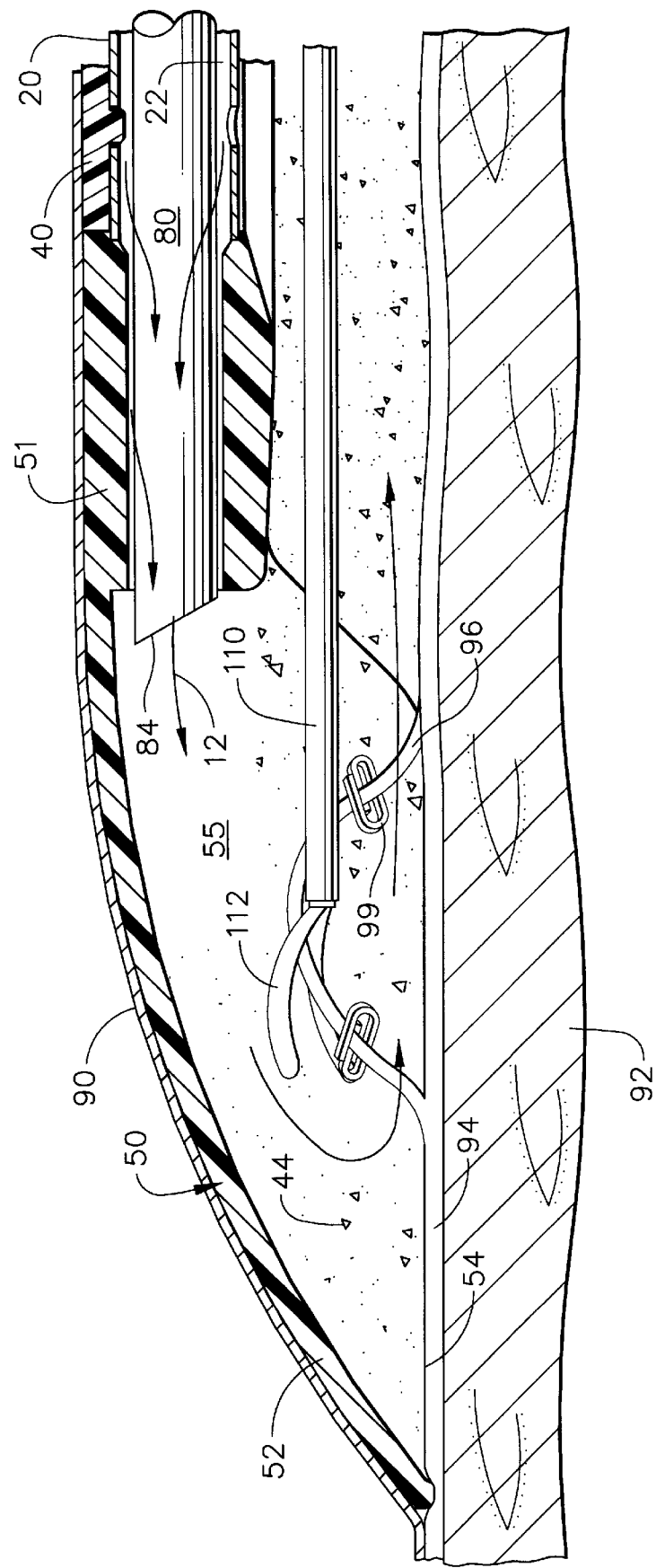
FIG. 6 is a fragmentary view in side elevation section of the distal end of the optical tissue dissector/retractor of FIG. 1 illustrating the flow of a fluid therethrough.

The working head 50 is made of a transparent material such as clear plastic or glass in order to facilitate viewing of the movement of the dissector/retractor 10 when placed in tissue 92 (FIG. 6). The optical working head 50 is generally concave and has a spoon-shaped configuration. The working head 50 consists of an outer surface 52 which terminates at a peripheral edge 54. The outer surface 52 and the peripheral edge 54 bound and define a working space 55. The working space 55 facilitates the introduction of instruments into the working space 55 in order to perform various steps of a surgical procedure.

Figure 2:
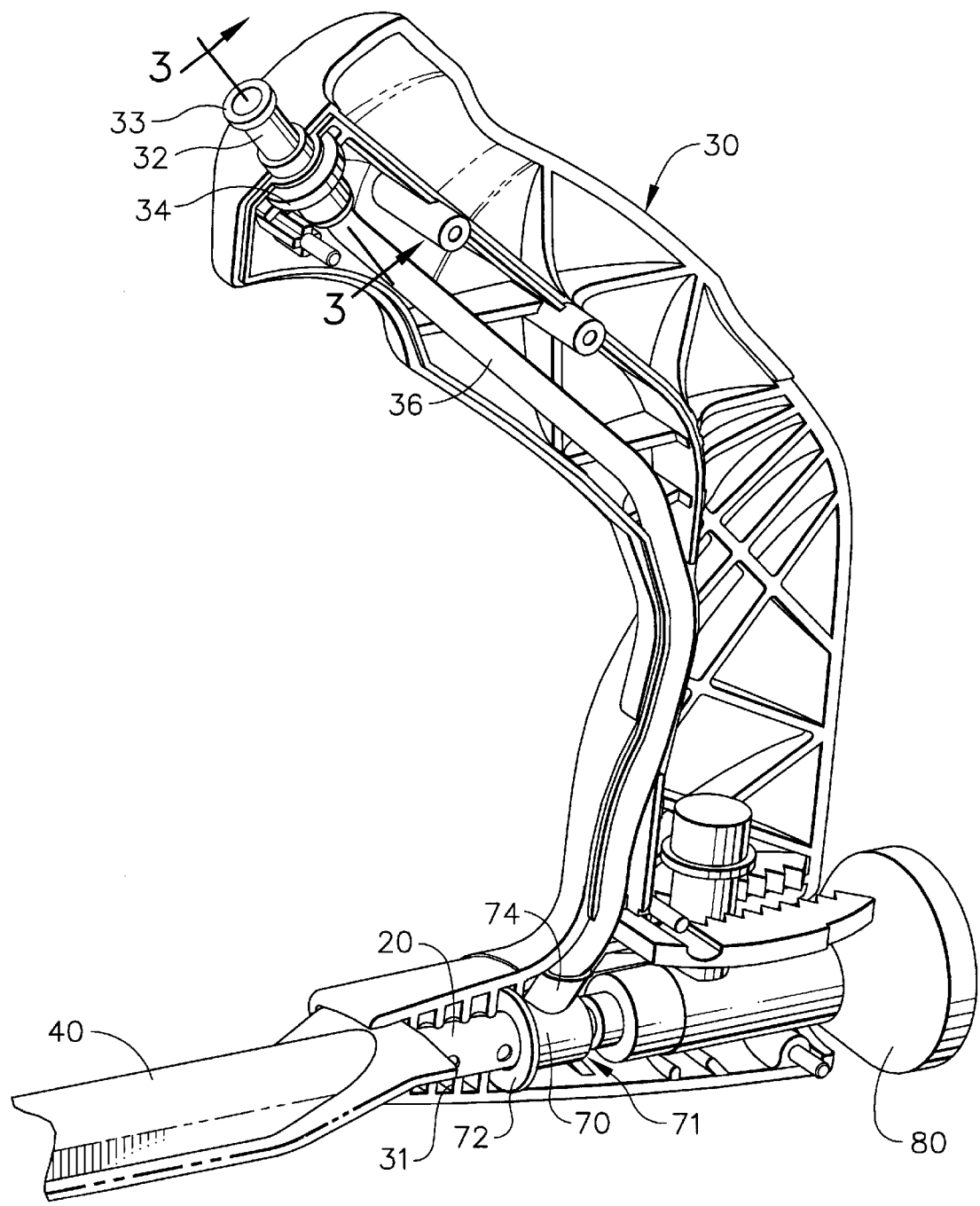
FIG. 2 is a perspective view of the proximal end of the optical tissue dissector/retractor of FIG. 1 with the handle partially broken away to reveal internal features.

A scope holder 20, which is a hollow tubular member, is connected to the handle 30 and supported by handle ribs 31 as best shown in FIG. 2. The scope holder 20 is positioned beneath the cover 40 and longitudinally extends parallel with the cover 40 to the working head 50 as shown in FIG. 6.

The scope holder 20 accommodates a conventional endoscope 80 which is positioned within the scope holder 20 by being placed into the proximal end of the scope holder 20 and positioned at the working head 50. The endoscope 80 includes an endoscope lens 84 located at a distal end thereof and is desirably positioned at the distal end of the scope holder such that the lens 84 is either adjacent or within the working space 55 of the working head 50.

Figure 5:
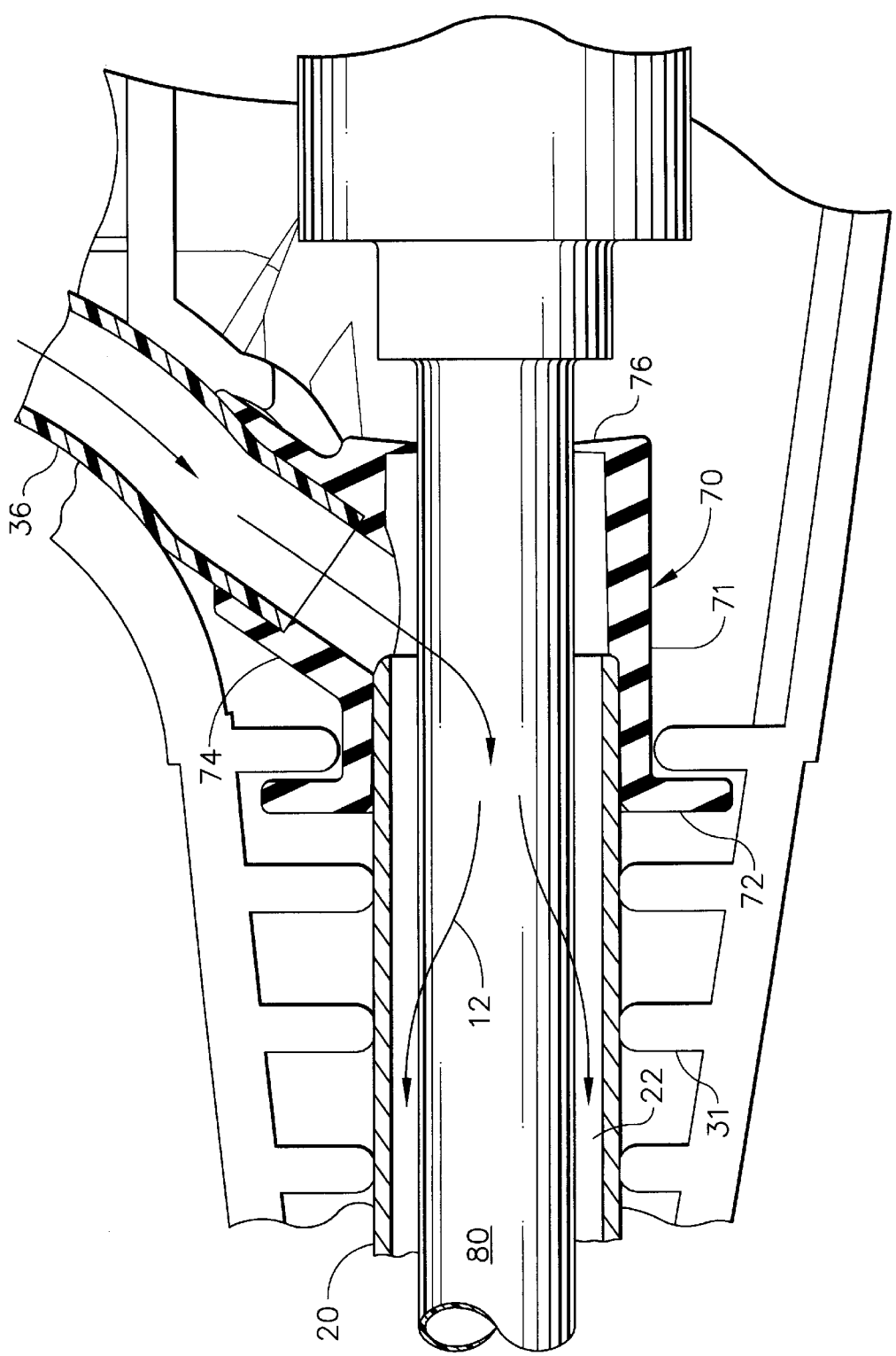
FIG. 5 is a fragmentary view in side elevation section illustrating a fluid flow at the scope seal of the optical tissue dissector/retractor of FIG. 1.

As best shown in FIGS. 5 and 6, the endoscope 80 has a diameter which is smaller than the diameter of the scope holder 20. Accordingly, a fluid flow gap 22 longitudinally extends between the proximal end and the distal end of the scope holder 20 and leads into or communicates with the working space 55 of the working head 50.

Figure 3:
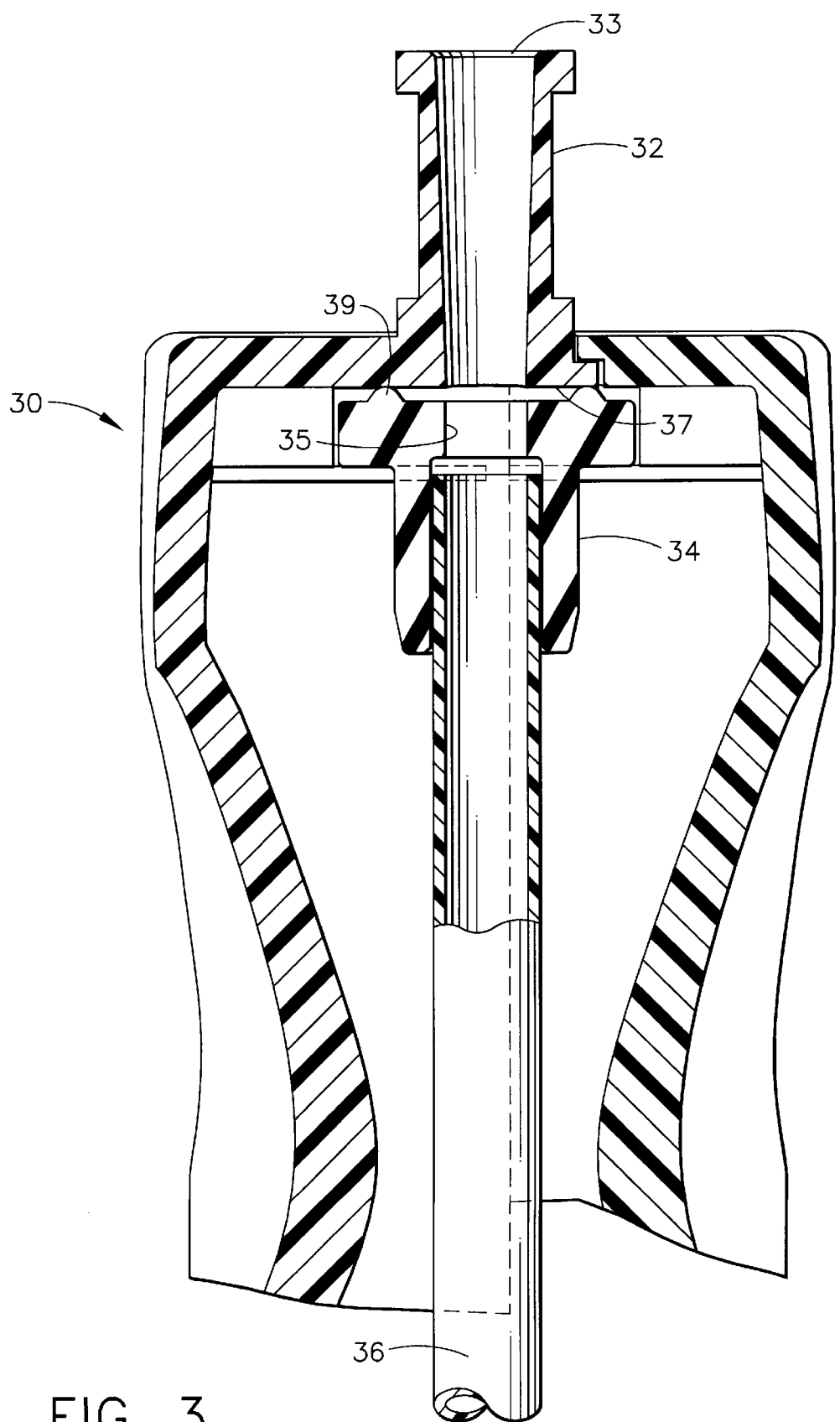
FIG. 3 is a transverse section view taken along line 3—3 of FIG. 2.

As best illustrated in FIG. 3, the handle 30 includes a luer lock connector 32 at the upper portion of the handle 30. The connector 32 is a hollow tubular member having a port 33 located an upper end of the connector 32. As will be described in greater detail below, the connector 32 is detachably connected to either a fluid irrigation source such as carbon dioxide carbon dioxide ($CO_2$) flow or a fluid aspiration source such as suction.

The handle 30 is sealed at its upper end by a luer seal 34. The luer seal 34 has a seal opening 35 and also includes a seal ring 39 which circumferentially surrounds the seal opening 35. The seal ring 39 is seated against a sealing surface 37 located adjacent the connector 32. A hollow purge tube 36 has an upper end which is sealingly secured by the luer seal 34 adjacent the seal opening 35. Accordingly, the purge tube 36 communicates with the seal opening 35 and the connector 32.

Figure 4:
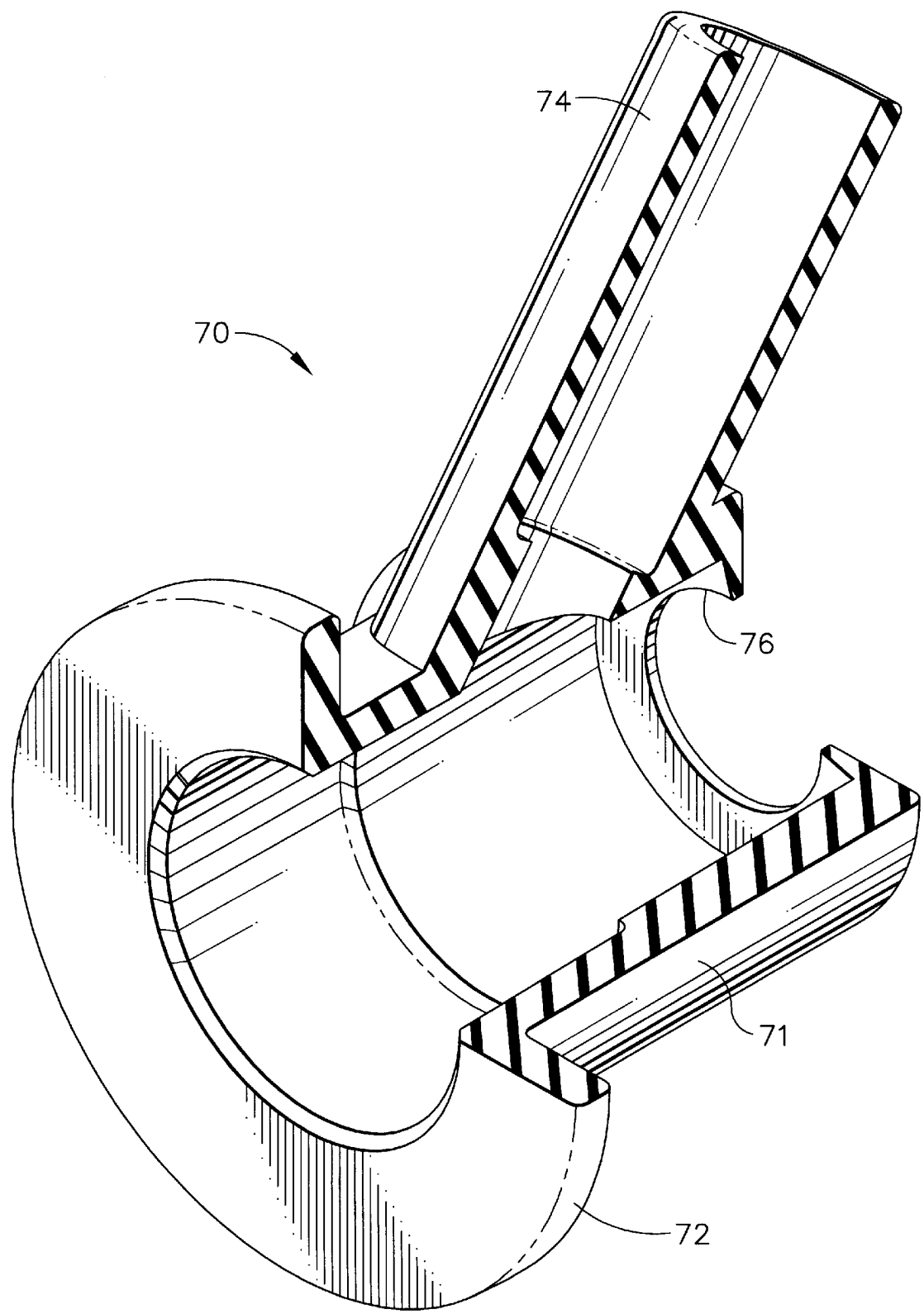
FIG. 4 is a perspective view of a scope seal partially broken away to reveal internal features.

The lower end of the purge tube 36 communicates with and is sealingly connected to a scope seal 70 (FIG. 4) as best shown in FIGS. 2 and 5. The scope seal 70 includes a seal body 71 having a purge tube adapter 74 located at an upper portion of the body 71. The purge tube adapter 74 seals against and communicates with the distal end of the purge tube 36 for sealing the purge tube 36 to the seal body 71. The seal 70 is positioned adjacent the scope holder 20 and is sealed against the scope holder 20 by a seal flange 72 which is circumferentially sealed around the outer surface of the scope holder 20.

The seal 70 also includes a diaphragm seal 76 opposite the seal flange 72. The diaphragm seal 76 circumferentially seals around the outer surface of the endoscope 80 upon insertion of the endoscope 80 through the scope seal 70 and into the scope holder 20 (FIG. 5).

The dissector/retractor 10 includes a particulate removal system such as a fluid carrying system comprising the connector 32, the purge tube 36 and the fluid gap 22 such that the particulate 44 can be cleared from the endoscope lens 84 and the working space 55 of the working head 50 as depicted in FIG. 6.

The fluid carrying system flushes or purges the particulate 44 from the endoscope lens 84 and the working space 55 with a fluid flow 12. Fluid flow 12 as defined herein designates any type of fluid such as a liquid or a gas that can effectively clear particulate 44 from the endoscope lens 84 and the working space 55. Some examples of the fluid flow 12 are $CO_2$ gas, air, nitrogen, water or a solution such as saline solution.

Figure 7:
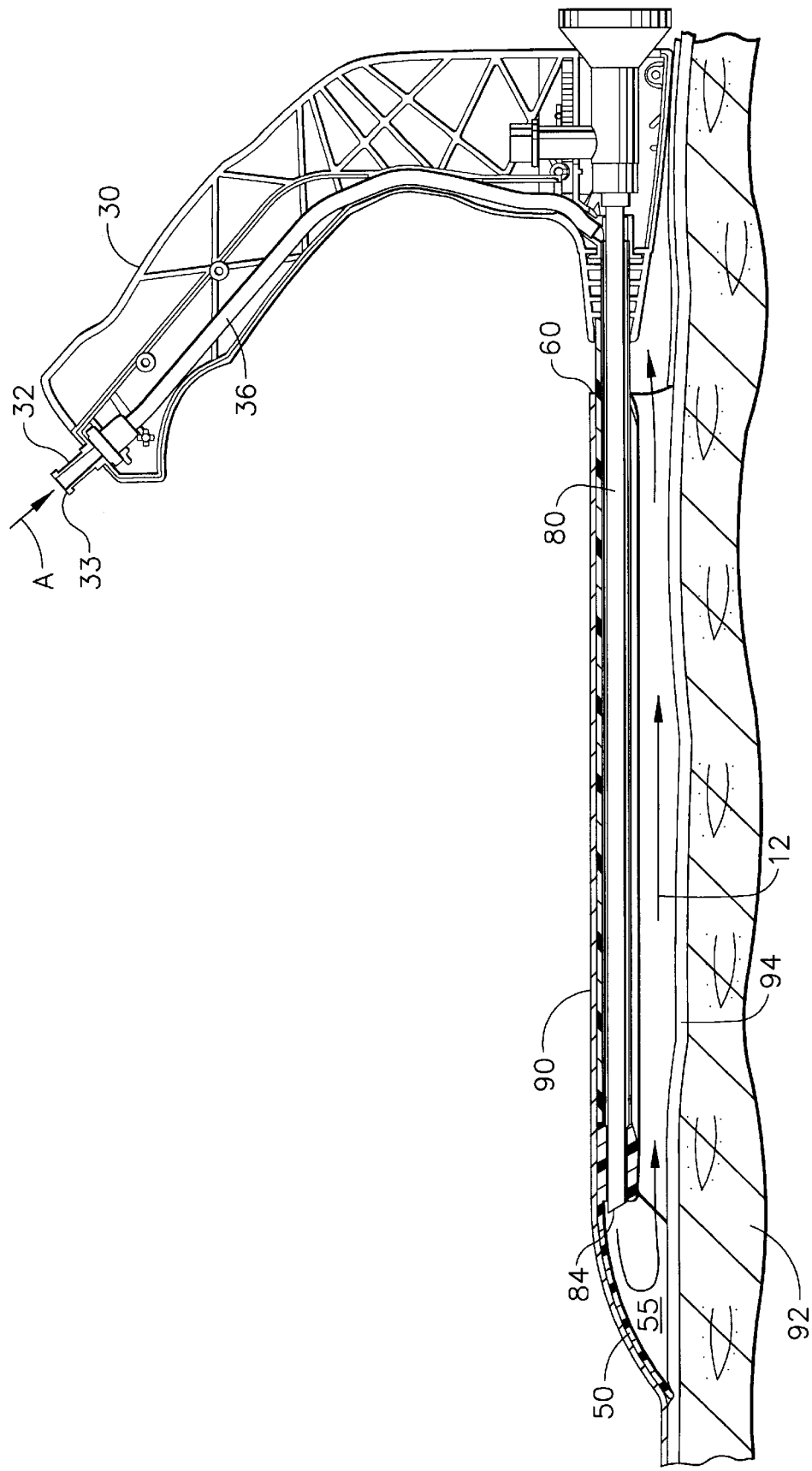
FIG. 7 is a side elevation view in section of the optical tissue dissector/retractor of FIG. 1 illustrating the flow of a fluid into the device through an entry port for purging particulate from the device while the device remains in tissue.

Moreover, the fluid carrying system according to the present invention allows for the fluid flow 12 to be provided into the dissector/retractor 10 from a fluid source such as $CO_2$ indicated at arrow A in FIG. 7. Likewise, fluid flow 12, such as air, can be withdrawn by aspiration from a suction source indicated at arrow B in FIG. 8. In either case, the particulate 44 is effectively purged and cleared from the endoscope lens 84 and the working space 55 of the working head 50.

Additionally, it is within the scope of the present invention to provide a fluid carrying system with alternative configurations. For instance, by providing a longer purge tube 36, the purge tube 36 could be provided into the working space 55 adjacent the endoscope lens 84 and secured to the dissector/retractor 10 in any number of ways.

METHOD OF USE

Figure 8:
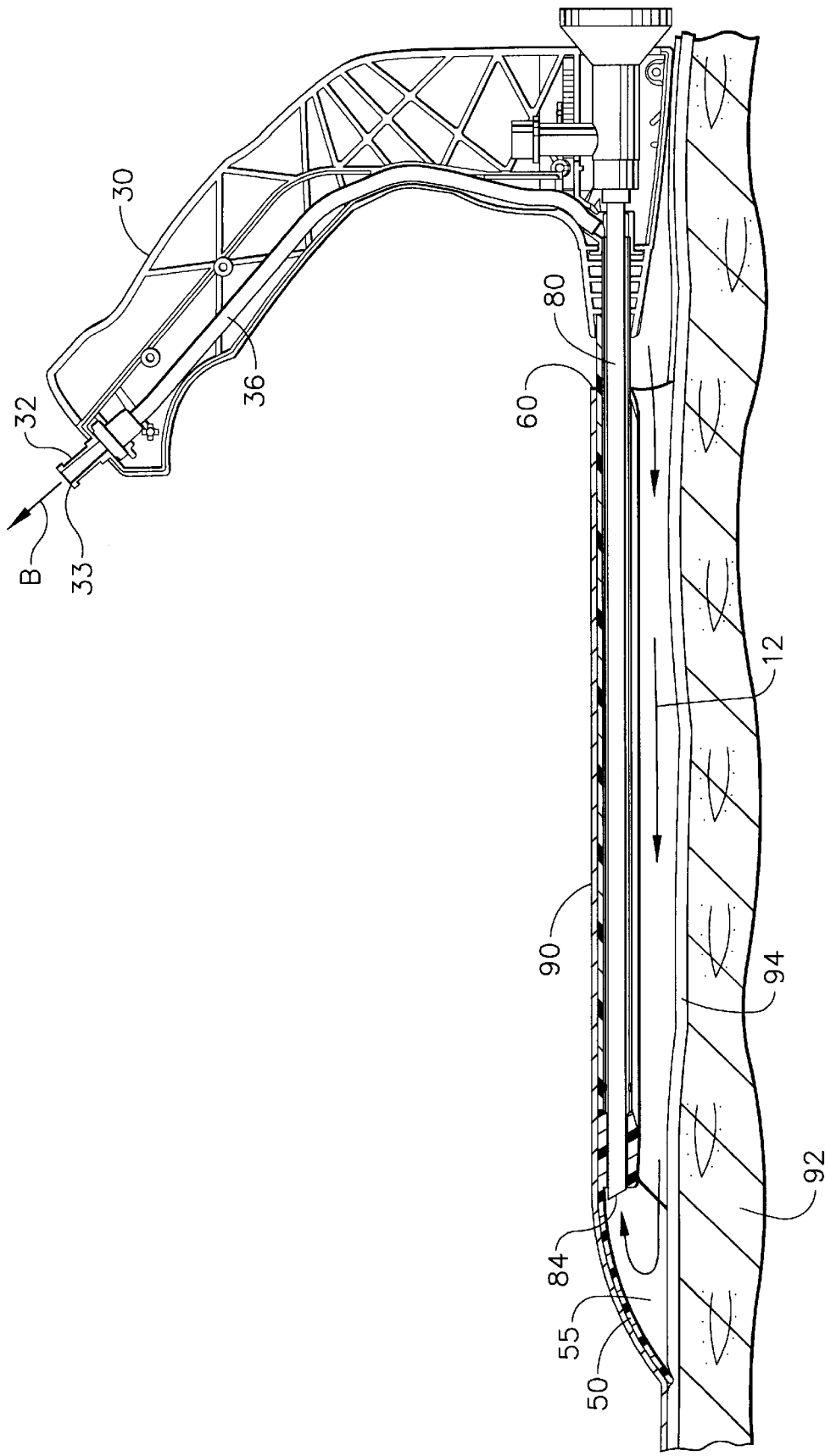
FIG. 8 is a side elevation view in section of the optical tissue dissector/retractor of FIG. 1 illustrating the flow of a fluid being purged from the device by suction through the entry port while the device remains in tissue.

The dissector/retractor 10 as outlined above and will be described in only one of the possible procedures that require tissue dissection or retraction or combination thereof. The procedure illustrated in FIGS. 6, 7 and 8 is a vessel harvest procedure such as a saphenous vein harvest procedure as part of a CABG procedure.

Prior to using the dissector/retractor 10, the surgeon places an incision 60 in the tissue 92. The surgeon then places the dissector/retractor 10 into the tissue 92 through the incision 60. Once placed in tissue 92, the surgeon maneuvers the dissector/retractor 10 through the tissue 92 over a vessel 94 which has been identified for harvesting.

As shown in FIG. 6, the dissector/retractor 10 is maneuvered through the tissue 92 over the vessel 94 in order to dissect and retract an upper tissue layer 90 away from the vessel 94. As a vessel side branch 96 is encountered, the working head 50 is positioned such that the side branch 96 is accessible in the working space 55. Clips 99 are placed on the side branch 96 in order to ligate the side branch to prevent bleeding once the side branch 96 is severed between the clips 99.

Once the side branch 96 has been ligated, a cutting instrument 110 having a least one cutting blade 112 is inserted into the working space 55 in order to sever the side branch 96. In many cases, the cutting instrument 110 is the ULTRACISION™ LCS Laparoscopic Coagulating Shears which is used to both cut and coagulate the side branch 96 simultaneously and thus, avoids the need for placing the clips 99. In some cases, the cutting instrument 110 is a pair of electrosurgical scissors.

Regardless of the type of cutting instrument 110 that is used, any particulate 44 produced an existing in the working space 55 and on the endoscope lens 84 is purged by the fluid flow 12. Particulate 44 is cleared from the dissector/retractor 10 by the fluid flow 12 provided through two purge modes. The first purge mode is a lavage mode and the second purge mode is an aspiration purge mode. Both of these purge modes are selected by the surgeon as a matter of preference. Additionally, besides selecting the type of purge mode for the dissector/retractor 10, the surgeon also has the option to provide either fluid flow 12 continuously or provide the fluid flow 12 at discrete intervals. As mentioned previously, the dissector/retractor 10 allows for the purging of the particulate 44 without having to remove the dissector/retractor 10 from the tissue 92.

FIG. 7 illustrates the dissector/retractor 10 being used in the lavage mode in which the fluid flow 12 is introduced into the dissector/retractor 10 through the port 33 of the connector 32 and into the purge tube 36 in handle 30 as indicated by arrow A. Upon exiting the distal end of the purge tube 36, the fluid flow 12 moves through the scope seal 70 and into the flow gap 22 between the scope holder 20 and endoscope 80 (FIG. 5) until reaching the working space 55 of the working head 50. Additionally, the fluid flow 12 purges or flushes the working space 55 and the endoscope lens 84 while continuing under the cover 40 and the scope holder 20 toward the proximal end of the dissector/retractor 10.

FIG. 8 illustrates the use of the dissector/retractor 10 in the aspiration mode. An aspiration source, such as vacuum or suction, is connected to the connector 32 at the port 33 and activated as indicated at arrow B. Accordingly, the fluid flow 12, which may consist mostly of air, is drawn from beneath the cover 40 and the scope holder 20 into the working space 55, past the endoscope lens 84 and through the flow gap 22. Thus, any particulate 44 existing in the working space 55 or on the endoscope lens 84 is withdrawn through the flow gap 22, the purge tube 36, and the connector 32 and out of the dissector/retractor 10 through the port 33.

Once the surgeon has completed the dissection and retraction of the upper tissue layer 90 from the tissue 92 and the vessel 94 has been freed and harvested, the dissector/retractor 10 can be withdrawn through the incision 60.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A surgical device for dissecting and retracting tissue comprising:
    a scope holder for holding an endoscope therein;
    a handle connected to said scope holder;
    a concave head connected to said scope holder, said concave head defining a working space therein; and
    a fluid carrying system operatively connected to and communicating with said concave head and said working space for clearing particulate from said working space, said fluid carrying system including a scope seal connected to a proximal end of said scope holder and a purge tube connected to said scope seal.

2. The surgical device according to claim 1, wherein said concave head is made of a transparent material.

3. The surgical device according to claim 2, wherein said scope seal and said purge tube are located in said handle.

4. The surgical device according to claim 3, wherein said fluid carrying system further includes a luer connector for connecting to a fluid source.

5. The surgical device according to claim 4, wherein said fluid carrying system further includes a luer seal located between said luer connector and said purge tube.

6. The surgical device according to claim 5, wherein said device further includes an endoscope positioned in said scope holder and sealed in said scope holder by said scope seal.

7. The surgical device according to claim 6, wherein said scope holder and said endoscope define a fluid gap therebetween.

8. The surgical device according to claim 7, wherein said fluid gap longitudinally extends from said proximal end of said scope holder to a distal end thereof.

9. The surgical device according to claim 8, wherein said device further includes a cover connected to said scope holder.

10. The surgical device according to claim 9, wherein said cover longitudinally extends along said scope holder from said handle to said concave head.

* * * * *